United States Patent [19]

Grollier et al.

[11] 4,402,977

[45] Sep. 6, 1983

[54] COMPOSITION FOR THE TREATMENT OF KERATIN FIBRES, BASED ON AMPHOTERIC POLYMERS AND ANIONIC POLYMERS

[75] Inventors: Jean F. Grollier; Claire Fiquet; Chantal Fourcadier, all of Paris; Claude Dubief, Versailles; Daniele Cauwet, Crosne, all of France

[73] Assignee: L'Oreal, Paris, France

[21] Appl. No.: 210,837

[22] Filed: Nov. 26, 1980

[30] Foreign Application Priority Data

Nov. 28, 1979 [FR] France ................ 79 29319

[51] Int. Cl.³ .................... A61K 7/09; A61K 7/11
[52] U.S. Cl. ........................ 424/70; 424/71
[58] Field of Search ............ 424/70, DIG. 1, DIG. 2, 424/71

[56] References Cited

U.S. PATENT DOCUMENTS 4,240,450 12/1980 Grollier et al. .................. 424/70

FOREIGN PATENT DOCUMENTS 1400366 5/1963 France .

2383660 10/1978 France ................ 424/70

*Primary Examiner*—Delbert R. Phillips
*Assistant Examiner*—F. J. Moezie
*Attorney, Agent, or Firm*—Fleit, Jacobson & Cohn

[57] ABSTRACT

The invention related to a composition used in the treatment of keratin substances which contains at least one amphoteric polymer containing units A and B randomly distributed in the polymer chain, where A denotes a unit derived from a monomer containing at least one basic nitrogen atom and B denotes a unit derived from an acid monomer containing one or more carboxyl or sulphonyl groups, or alternatively A and B can denote a cationic polymer chain containing secondary or tertiary amine groups or quaternary ammonium groups, in which chain at least one of the amine groups carries a carboxyl or sulphonyl group joined via a hydrocarbon radical, or alternatively A and B form part of a chain of a polymer with alpha, beta-dicarboxyethylene units, in which one of the carboxyl groups has been reacted with a polyamine containing one or more primary, secondary or tertiary amine groups, and at least one anionic polymer containing one or more carboxyl or sulphonyl groups.

21 Claims, No Drawings

COMPOSITION FOR THE TREATMENT OF KERATIN FIBRES, BASED ON AMPHOTERIC POLYMERS AND ANIONIC POLYMERS

The present invention relates to compositions, in particular cosmetic compositions, which are intended for use in the treatment of keratin fibres and in particular hair.

Anionic polymers have been recommended for use in hair-treatment compositions, in particular for imparting certain properties such as the toughness of the keratin fibre, the hold of the head of hair and the gloss. They are most frequently used without rinsing after they have been applied to the head of hair.

However, these anionic polymers exhibit the disadvantage of poor attachment to the keratin fibres and are easily removed on rinsing, or, in the absence of rinsing, give rise to the formation of powder as a result of an excessively high friability and poor substantivity.

To overcome this disadvantage, it has already been proposed to use cationic polymers with the anionic polymers. An association of this type is described, in particular, in French Pat. No. 2,383,660.

However, we have found that, although the association of an anionic polymer and a cationic polymer makes it possible to impart, in particular, remarkable cosmetic properties to the hair, successive treatments with this association lead to rough hair or to excessive covering of the fibres, in particular in the case of sensitized hair.

This rough or hair-covering character after several treatments seem essentially to be due to the selective removal of the anionic polymer, which, following several treatments, causes the deposition of several layers of cationic polymers although we do not wish to be limited by this theory.

We have now discovered, according to the present invention, that, by using certain amphoteric polymers in place of the cationic polymer, the keratin fibres exhibit a good hold with time and are supple, soft and glossy, even after several applications of these compositions.

It has been possible to observe particularly valuable results for treatments usually followed by rinsing, such as shampoo treatments, and treatments with lotions or creams which are used to obtain a conditioning effect on the hair when applied before or after colouring, bleaching, shampooing or perming.

We have discovered that, by using certain amphoteric polymers with anionic polymers, remarkable holding properties can be imparted to the hair without causing the cosmetic disadvantages of selective removal.

Accordingly the present invention provides a composition intended for use in the treatment of keratin fibres, which contains at least one anionic polymer and at least one amphoteric polymer, as specified below, as well as a process for the treatment of keratin fibres, using an anionic polymer and an amphoteric polymer; in particular it is a process for attaching an anionic polymer to keratin fibres by means of an amphoteric polymer.

The compositions according to the present invention are essentially characterised in that they comprise, in a suitable medium permitting the application of the polymers to the keratin fibres:

(a) at least one anionic polymer containing one or more carboxyl or sulphonyl groups, and
(b) at least one amphoteric polymer containing units A and B randomly distributed in the polymer chain, where A denotes a unit derived from a monomer containing at least one basic nitrogen atom and B denotes a unit derived from an acid monomer containing one or more carboxyl or sulphonyl groups, or alternatively A and B can denote groups derived from a zwitterionic carboxybetaine monomer; A and B can also denote a cationic polymer chain containing secondary amine groups, tertiary amine groups which are different from a piperazinyl group, or quaternary ammonium groups, in which chain at least one of the amino groups carries a carboxyl or sulphonyl group joined via a hydrocarbon radical, or alternatively A and B form part of a polymer with alpha, beta-dicarboxyethylene units, in which one of the carboxyl groups has been reacted with a polyamine containing one or more primary, secondary or tertiary amine groups, with the proviso that when A and B form a cationic polymer chain comprising polyaminoamide units in which at least one of the amino groups is substituted by a sulphonic or carboxylic acid group via an intermediate hydrocarbon radical, the anionic polymer is not a vinyl acetate/crotonic acid copolymer.

The amphoteric polymers, corresponding to this definition, which are most particularly preferred are chosen from amongst the following polymers:

(1) the polymers resulting from the copolymerisation of a vinyl monomer carrying a carboxyl group, such as acrylic acid, methacrylic acid, maleic acid or alpha-chloroacrylic acid, and a basic monomer which is a substituted vinyl compound containing at least one basic nitrogen atom, such as dialkylaminoalkyl methacrylates and acrylates and dialkylaminoalkylmethacrylamides and -acrylamides. Products of this type are described in U.S. Pat. No. 3,836,537.

(2) the polymers containing units derived from
(a) at least one monomer chosen from amongst acrylamides or methacrylamides substituted on the nitrogen by an alkyl radical,
(b) at least one acid comonomer containing one or more reactive carboxyl groups, and
(c) at least one basic comonomer, such as esters, with primary, secondary and tertiary amine substituents and quarternary ammonium substituents, of acrylic and methacrylic acids, and the product resulting from the quaternisation of dimethylaminoethyl methacrylate with dimethyl or diethyl sulphate.

The N-substituted acrylamides or methacrylamides which are most particularly preferred are the groups in which the alkyl radicals contain from 2 to 12 carbon atoms, especially N-ethylacrylamide, N-tert.-butylacrylamide, N-tert.-octylacrylamide, N-octylacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates.

(3) the crosslinked and alkylated polyaminoamides partially or totally derived from polyaminoamides of the general formula:

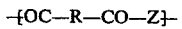

(I)

in which R represents a divalent radical derived from a saturated dicarboxylic acid, from a monocarboxylic or dicarboxylic aliphatic acid with an ethylenic double bond, or from an ester of a lower alkanol having 1 to 6 carbon atoms and of these acids or of a radical derived from the addition of any one of the said acids onto a bis-primary or bis-secondary amine, and Z denotes a radical of a bis-primary or mono- or bis-secondary polyalkylene-polyamine, and preferably represents:

(1) in proportions of 60 to 100 mol %, the radical

$$-\text{[NH}-(CH_2)_x-\text{NH]}_n \quad (II)$$

in which x=2 and n=2 or 3 or alternatively x=3 and n=2, this radical being derived from diethylenetriamine, triethylenetetramine or dipropylenetriamine;

(2) in proportions of 0 to 40 mol %, the above radical (II) in which x=2 and n=1 and which is derived from ethylenediamine, or the radical

derived from piperazine; and (3) in proportions of 0 to 20 mol %, the radical $-\text{NH}-(CH_2)_6-\text{NH}-$, derived from hexamethylenediamine, these polyaminoamides being crosslinked by the addition of a difunctional crosslinking agent chosen from amongst epihalogenohydrins, diepoxides, dianhydrides, and bis-unsaturated derivatives, using 0.025 to 0.35 mol of crosslinking agent per amine group of the polyaminoamide, and being alkylated by reaction with acrylic acid, chloroacetic acid or an alkane-sultone or their salts.

The saturated carboxylic acids are preferably chosen from amongst acids having 6 to 10 carbon atoms, such as adipic acid, 2,2,4- and 2,4,4-trimethyladipic acids, terephthalic acid and acids with an ethylenic double bond, such as acrylic, methacrylic and itaconic acids.

The alkane-sultones used in the alkylation are preferably propane- or butane-sultone, and the salts of the alkylating agents are preferably the sodium or potassium salts.

(4) the polymers containing zwitterionic units derived from the formula:

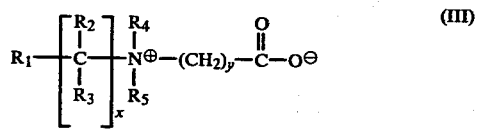

in which $R_1$ denotes a polymerisable unsaturated group, such as an acrylate, methacrylate, acrylamide or methacrylamide group, x and y independently represent an integer from 1 to 3, $R_2$ and $R_3$ independently represent hydrogen, methyl, ethyl or propyl, and $R_4$ and $R_5$ independently represent a hydrogen atom or an alkyl radical such that the sum of the carbon atoms in $R_4$ and $R_5$ does not exceed 10.

The polymers containing units of this type can also contain units derived from non-zwitterionic monomers, such as vinylpyrrolidone, dimethylaminoethyl or diethylaminoethyl acrylate or methacrylate or alkyl acrylates or methacrylates, acrylamides or methacrylamides, or vinyl acetate.

(5) the polymers derived from chitosan and containing monomer units corresponding to the following formulae:

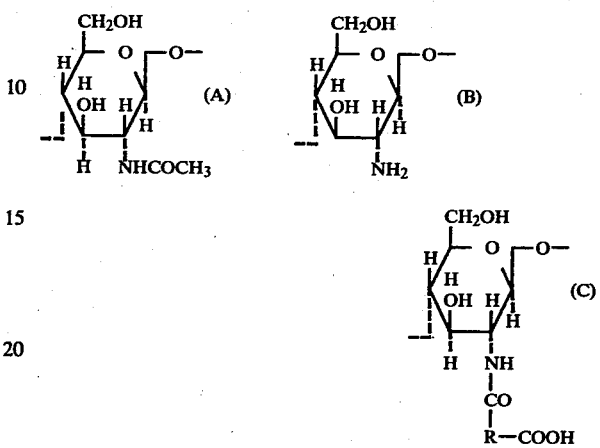

in which the unit A is present in proportions of 0 to 30%, B is present in proportions of 5 to 50% and C is present in proportions of 30 to 90%. In the formula C, R represents a radical of the formula:

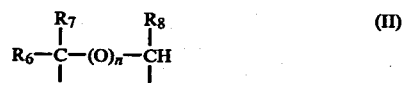

in which, if n=0, $R_6$, $R_7$ and $R_8$, which are identical or different, each represent a hydrogen atom, a methyl, hydroxyl, acetoxy or amino radical, a monoalkylamino radical or a dialkylamino radical, which is optionally interrupted by one or more nitrogen atoms and/or optionally substituted by one or more amine, hydroxyl, carboxyl, alkylthio or sulphonyl groups; or an alkylthio radical in which the alkyl group carries an amino radical, at least one of the radicals $R_6$, $R_7$ and $R_8$ in this case being a hydrogen atom, or, if n is equal to 1, $R_6$, $R_7$ and $R_8$ each represent a hydrogen atom. The salts formed by these compounds with bases or acids are also included.

(6) the polymers corresponding to the general formula IV and described in French Pat. No. 1,400,366:

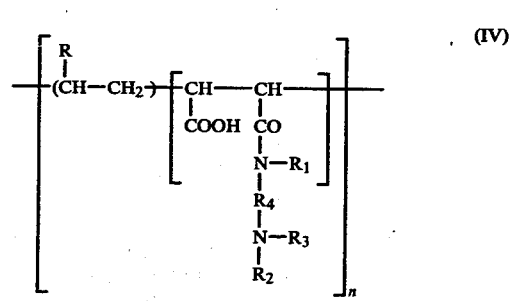

in which R represents a hydrogen atom or a $CH_3O$, $CH_3CH_2O$ or phenyl radical, $R_1$ denotes hydrogen or a lower alkyl radical, such as methyl or ethyl, $R_2$ denotes hydrogen or a lower alkyl radical, such as methyl or ethyl, $R_3$ denotes a lower alkyl radical, such as methyl or ethyl, or a radical corresponding to the formula:

$R_4-N(R_2)_2$, where $R_4$ represents a group —$CH_2$—$CH_2$—, —$CH_2$—$CH_2$—$CH_2$— or

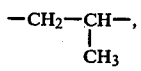

and also the higher homologues of these radicals containing up to 6 carbon atoms.

The amphoteric polymers used according to the invention generally have a molecular weight of 500 to 2 million. The preferred polymers are those of groups 2, 4, 5 and 6.

The anionic polymers which are more particularly preferred for use in the invention are water-soluble polymers, it being possible to obtain this solubility by neutralising the acid groups with an alkali, such as sodium hydroxide or potassium hydroxide, or an amine, such as triethanolamine, 2-amino-2-methylpropan-1-ol or 2-amino-2-methylpropane-1,3-diol. These polymers generally have a molecular weight of 500 to 5 million.

The carboxyl groups can be provided by unsaturated monocarboxylic or dicarboxylic acids such as those corresponding to the formula:

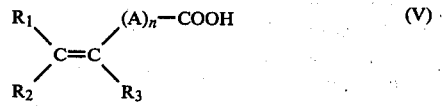

in which n is 0 or an integer from 1 to 10, A denotes a methylene group joined either directly to the carbon atom of the unsaturated group, or to an adjacent methylene group if n is greater than 1, via a hetero-atom, such as oxygen or sulphur, $R_1$ denotes a hydrogen atom or a phenyl or benzyl group, $R_2$ denotes a hydrogen atom or a lower alkyl or carboxyl group, and $R_3$ denotes a hydrogen atom or a lower alkyl, —$CH_2$—COOH, phenyl or benzyl group.

In the abovementioned formula, a lower alkyl radical preferably denotes a group having 1 to 4 carbon atoms, and in particular methyl or ethyl.

The anionic polymers which are preferred according to the invention are:

acrylic or methacrylic acid homopolymers or copolymers or their salts, and in particular the products sold under the names VERSICOL E or K by ALLIED COLLOID, ULTRAHOLD 8 by CIBA GEIGY and DARVAN No. 7 by Van der BILT, the acrylic acid/acrylamide copolymers sold, in the form of their sodium salt, under the names RETEN 421, 423 or 425 by HERCULES, and the acrylic or methacrylic acid/vinyl alcohol copolymers sold under the name HYDAGEN F by HENKEL;

the copolymers of the abovementioned acids with a monoethylenic unsaturated monomer, such as ethylene, vinylbenzene, vinyl or allyl esters or acrylic or methacrylic acid esters, which copolymers are optionally grafted onto a polyalkylene glycol, such as polyethylene glycol, and optionally crosslinked (polymers of this type are described, in particular, in French Pat. No. 1,222,944 and German Application 2,330,956); and the copolymers of this type which contain an optionally N-alkylated and/or N-hydroxyalkylated acrylamide unit in their chain, such as those described, in particular, in Luxembourg Patent Applications 75,370 and 75,371 or sold under the name QUADRAMER 5 by American Cyanamid;

the copolymers derived from crotonic acid, such as those which contain, in their chain, vinyl acetate or propionate units and optionally other monomers, such as the allyl or methallyl ester, vinyl ether or vinyl ester of a saturated carboxylic acid with a long hydrocarbon chain, such as those containing at least 5 carbon atoms. These polymers can optionally be grafted and cross-linked. Polymers of this type are described, inter alia, in French Pat. Nos. 1,222,944, 1,580,545, 2,265,782, 2,265,781 and 1,564,110. Commercial products included in this class are the 28-29-30 and 26-13-14 resins sold by National Starch;

the polymers derived from maleic, fumaric or itaconic acids or anhydrides with vinyl esters, vinyl ethers, vinyl halides, phenylvinyl derivatives, and acrylic acid and its esters; these polymers can be esterified. Polymers of this type are described, in particular, in U.S. Pat. Nos. 2,047,398, 2,723,248 and 2,102,113 and British Specification No. 839,805, in particular those sold under the names GANTREZ AN or ES by General Anilin or EMA 1325 by MONSANTO. Polymers also included in this class are the copolymers of maleic, citraconic or itaconic anhydrides and an allyl or methallyl ester, which optionally contain an acrylamido or methacrylamido group in their chain and are monoesterified or mono-amidated, the said copolymers being described in French Patent Applications 76/13,929 and 76/20,917;

the salts of polystyrenesulphonic acid, such as the sodium salts sold by National STARCH under the name Flexan 500 and having a molecular weight of about 500,000, or under the name Flexan 130 and having a molecular weight of about 100,000. Products of this type are described, in particular, in French Pat. No. 2,198,729, which is hereby incorporated by reference;

the alkali metal or alkaline earth metal salts of the sulphonic acids derived from lignin, and more particularly the calcium or sodium lignosulphonates, such as the product sold under the name Marasperse C-21 by American Can Co and the $C_{10}C_{14}$ products sold by Avebene; and the polymers containing salified alkylnaphthalenesulphonic acid units, such as the sodium salt sold under the name Darvan No. 1 by Van der Bilt.

The amphoteric polymers of group (3) are used with anionic polymers described above other than the vinyl acetate/crotonic acid copolymer, and in particular the polymers with acrylic or methacrylic acid units, the terpolymers with crotonic acid groups, the polymers derived from maleic, fumaric or itaconic acid or anhydride and the polymers derived from sulphonic acid.

The associations or combinations which are more particularly preferred within the scope of the present invention are those using the amphoteric polymers of group (2) or group (5) with the following anionic polymers:

the acrylic or methacrylic acid homopolymers or copolymers or their salts, the polymers derived from maleic acid or anhydride, and the salts of polystyrenesulphonic acid.

Associations which have given particularly valuable results are those comprising the polymer sold under the name AMPHOMER with the anionic polymers sold under the names Gantrez ES 425, Hydagen F, Versicol E5, Versicol K11 and Flexan.

The compositions preferably do not contain other polymers and in particular do not contain a cationic polymer.

The polymers used according to the invention are typically present in the compositions in proportions from 0.01 to 10% by weight and preferably from 0.5 to 5% by weight. The pH of these compositions is generally from 2 to 11, especially from 3 to 10 and preferably from 4 to 8.5.

These compositions are preferably used for treating human hair and can be presented in various forms, such as a liquid, a cream, an emulsion or a gel. In addition to water, they can contain any cosmetically acceptable solvent chosen, in particular, from amongst monoalcohols, such as alkanols having 1 to 8 carbon atoms, for example ethanol and isopropanol, benzyl alcohol and phenylethyl alcohol, and polyalcohols, such as alkylene glycols, for example ethylene glycol and propylene glycol, and glycol ethers, such as mono-, di- and triethylene glycol monoalkyl ethers, for example ethylene glycol monomethyl ether, ethylene glycol monoethyl ether and diethylene glycol monoethyl ether, used singly or in a mixture. These solvents are generally present in proportions which are less than or equal to 70% by weight, relative to the weight of the total composition.

These compositions can also contain electrolytes and, amongst these, those which are more particularly preferred are alkali metal salts, such as the sodium, potassium or lithium salts. These salts are preferably halides, such as the chloride or bromide, sulphates, or the salts of organic acids, such as the acetates or lactates.

These compositions can also be in the form of a powder to be diluted before use.

Those compositions of which the usual applications are followed by rinsing are preferred and give the most surprising results.

In particular, they can be in the form of a shampoo, a rinsing lotion, a cream or a treating product, which can applied before or after colouring or bleaching, before or after shampooing or before or after perming, and they can also take the form of, for example, colouring products, wavesetting lotions, brushing lotions and bleaching, perming and straightening products.

A preferred embodiment is one in which the composition is in the form of a shampoo. In this case, in addition to the abovementioned polymers, the compositions according to the invention contain at least one anionic, non-ionic, cationic or amphoteric surface-active agent or mixtures thereof.

Amongst the anionic surface-active agents, there may be mentioned, in particular, the following compounds and also mixtures thereof: the alkali metal salts, the ammonium salts, the amine salts or the aminoalcohol salts of the following compounds: alkyl-sulphates, alkyl-ether-sulphates, alkylamide-sulphates and alkylamide-ether-sulphates, alkylaryl-polyether-sulphates and monoglyceridesulphates; alkylsulphonates; alkylamide-sulphonates, alkylarylsulphonates and alpha-olefine-sulphonates; alkylsulphosuccinates, alkyl-ether-sulphosuccinates and alkylamide-sulphosuccinates; alkyl-sulphosuccinamates; alkyl-sulphoacetates and alkyl-polyglycerol-carboxylates; alkyl-phosphates and alkyl-ether-phosphates; alkylsarcosinates, alkylpolypeptidates, alkylamidopolypeptidates, alkylisethionates and alkyltaurates, the alkyl radical in all these compounds being a linear chain having 12 to 18 carbon atoms, and fatty acids, such as oleic acid, ricinoleic acid, palmitic acid, stearic acid, acids derived from copra oil or from hydrogenated copra oil, and carboxylic acids of polyglycol ethers, corresponding to the formula:

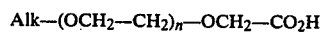

$$Alk-(OCH_2-CH_2)_n-OCH_2-CO_2H$$

in which the substituent Alk corresponds to a linear chain having from 12 to 18 carbon atoms and in which n is an integer from 5 to 15.

Amongst the anionic surface-active agents, those which are more particularly preferred are: sodium lauryl-sulphate, ammonium lauryl-sulphate or triethanolamine lauryl-sulphate, the sodium salt of sulphated lauryl alcohol oxyethyleneated with, say, 2.2 mols of ethylene oxide, the triethanolamine salt of lauroyl-keratinic acid, the triethanolamine salt of the product resulting from the condensation of copra acids and animal protein hydrolysates, and the products of the formula:

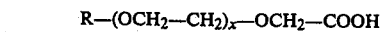

$$R-(OCH_2-CH_2)_x-OCH_2-COOH$$

in which R is generally a $C_{12}$ to $C_{14}$ alkyl radical and x varies from 6 to 10.

Amongst the non-ionic surface-active agents which can optionally be used in a mixture with the above-mentioned anionic surface-active agents, there may be mentioned, in particular, the products resulting from the condensation of a monoalcohol, and alpha-diol, an alkylphenol, an amide or a diglycolamide with glycidol, such as the products corresponding to the formula:

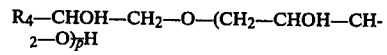

$$R_4-CHOH-CH_2-O-(CH_2-CHOH-CH_2-O)_pH$$

in which $R_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p represents an average statistical value of 1 to 10, as described in French Pat. No. 2,091,516; products corresponding to the formula:

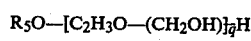

$$R_5O-[C_2H_3O-(CH_2OH)]_qH$$

in which $R_5$ denotes an alkyl, alkenyl or alkylaryl radical and q has an average statistical value of 1 to 10, such as the compounds described in French. Pat. No. 1,477,048; and products corresponding to the formula:

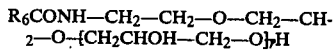

$$R_6CONH-CH_2-CH_2-O-CH_2-CH_2-O-(CH_2CHOH-CH_2-O)_rH$$

in which $R_6$ denotes a saturated or unsaturated, linear or branched aliphatic radical, or a mixture of such radicals, which can optionally contain one or more hydroxyl groups, has 8 to 30 carbon atoms and is of natural or synthetic origin, and r represents an integer or decimal number from 1 to 5 and denotes the average degree of codensation, such as the compounds described in French Patent Specification No. 2,328,763.

Other compounds included in this class are polyoxyethyleneated or polyglycerolated alcohols, alkylphenols or fatty acids with linear fatty chains containing 8 to 18 carbon atoms. There may also be mentioned copolymers of ethylene oxide and propylene oxide, products resulting from the condensation of ethylene oxide and propylene oxide with fatty alcohols, polyoxyethyleneated fatty amides, polyoxyethyleneated fatty amines, ethanolamides, fatty acid esters of glycol, fatty acid esters of sorbitol and fatty acid esters of sucrose.

Amongst these non-ionic surface-active agents, those which are more particularly preferred correspond to the formula:

$$R_4-CHOH-CH_2-O-(CH_2-CHOH-CH_2-O)_p-H$$

in which $R_4$ denotes a mixture of alkyl radicals having 9 to 12 carbon atoms and p has a statistical value of, say, 3.5, to the formula:

$$R_5-O-[C_2H_3O(CH_2OH)]_q-H$$

in which $R_5$ denotes $C_{12}H_{25}$ and q has a statistical value of 4 to 5, and to the formula:

$$R_6-CONH-CH_2-CH_2-O-CH_2-CH_2-O-[CH_2CHOH-CH_2O]_r-H$$

in which $R_6$ denotes a mixture of radicals derived from lauric, myristic, oleic and copra acids and r has a statistical value of 3 to 4.

The preferred polyoxyethyleneated or polyglycerolated fatty alcohols are oxyethyleneated oleyl alcohol containing 10 mols of ethylene oxide, oxyethyleneated lauryl alcohol containing 12 mols of ethylene oxide, oxyethyleneated nonylphenol containing 9 mols of ethylene oxide, polyglycerolated oleyl alcohol containing 4 mols of glycerol and polyoxyethyleneated sorbitan monolaurate containing 20 mols of ethylene oxide.

Amongst the cationic surface-active agents which can be used by themselves or in a mixture, there may be mentioned, in particular, fatty amine salts, such as alkylamine acetates, quaternary ammonium salts, such as alkyldimethylbenzylammonium, alkyltrimethylammonium, alkyldimethylhydroxyethylammonium and dimethyldistearylammonium chlorides and bromides, alkylaminoethyltrimethylammonium methosulphates and alkylpyridinium salts, and imidazole derivatives. The alkyl radicals in these compounds preferably have 1 to 22 carbon atoms. Compounds of cationic character, such as amine oxides, for example alkyldimethylamine oxides or alkylaminoethyldimethylamine oxides, may also be mentioned.

Amongst the amphoteric surface-active agents which can be used, there may be mentioned, more particularly, alkylamino-monopropionates and -dipropionates, betaines, such as N-alkylbetaines, N-alkylsulphobetaines and N-alkylaminobetaines, cycloimidinium compounds, such as alkylimidazolines, and asparagine derivatives. The alkyl group in these surface-active agents preferably has 1 to 22 carbon atoms.

In these shampoos, the concentration of surface-active agent is generally 3 to 50% by weight and preferably 3 to 20% and the pH is generally 3 to 10.

Another preferred embodiment is one in which the composition is in the form of a rinsing lotion to be applied mainly before or after shampooing. These lotions are usually aqueous or aqueous-alcoholic solutions, or emulsions, thickened lotions or gels.

If the compositions are presented in the form of emulsions, they can be non-ionic or anionic. The non-ionic emulsions mainly consist of a mixture of an oil and/or a fatty alcohol with a polyoxyethyleneated alcohol, such as polyoxyethyleneated stearyl or cetyl/stearyl alcohols. Cationic surface-active agents, such as those defined above, can be added to these compositions.

The anionic emulsions are essentially made from soap.

If the compositions are presented in the form of thickened lotions or of gels, they contain thickeners in the presence or absence of solvents. The thickeners which can be used include sodium alginate, gum arabic or cellulose derivatives, such as methylcellulose, hydroxymethylcellulose, hydroxyethylcellulose, hydroxypropylcellulose or hydroxypropylmethylcellulose. It is also possible to thicken the lotions with a mixture of polyethylene glycol and polyethylene glycol stearate or distearate or with a mixture of a phosphoric acid ester and an amide. The concentration of thickener is generally from 0.5 to 30% by weight and preferably from 0.5 to 15% by weight. The pH of the rinsing lotions is generally from 3 to 9.

If the compositions according to the invention are presented in the form of styling lotions, shaping lotions or so-called wavesetting lotions, these lotions generally comprise, in aqueous, alcoholic or aqueous-alcoholic solution, the components of the association defined above and also, optionally, non-ionic polymers and anti-foam agents.

If the compositions of the present invention constitute dyeing compositions for keratin fibres, they contain, in addition to the amphoteric polymer (or polymers) and the anionic polymer (or polymers), at least one oxidation dyestuff precursor and/or one direct dyestuff, and optionally various adjuvants which make it possible to present them in the form of a cream, gel or solution described above.

The compositions can also contain antioxidants, sequestering agents or other adjuvant normally used in this type of composition.

The oxidation dyestuff precursors are aromatic compounds of the diaminobenzene or diaminopyridine, aminophenol or phenol type. These precursors include, on the one hand, the dyestuff precursors of the "para" type and the dyestuff precursors of the "ortho" type, chosen from diaminobenzenes, diaminopyridines, aminophenols and diphenylamines, and, on the other hand, the couplers, which are "meta" derivatives chosen from meta-diaminobenzenes, meta-diaminopyridines, meta-aminophenols, meta-diphenols, phenols and naphthols.

Amongst the direct dyestuffs, there may be mentioned azo dyestuffs, anthraquinone dyestuffs, nitro benzene derivatives, indamines, indophenols and indoanilines.

The pH of these dyeing compositions is generally 7 to 11; it can be adjusted to the desired value by adding an alkalising agent, such as ammonia, alkali metal hydroxides, alkali metal and ammonium carbonates, alkylamines, alkanolamines or a mixture thereof.

Finally, the association according to the invention can be used in compositions intended for waving or straightening the hair. In addition to the amphoteric polymer (or polymers) and the anionic polymer (or polymers), this composition contains one or more reducing agents and optionally other adjuvants normally used in this type of composition, and it is used with a neutralising composition.

The reducing agents are typically sulphites and mercaptans and more particularly thioglycolates or thiolactates or a mixture thereof.

The neutralising composition contains an oxidising agent such as hydrogen peroxide and alkali metal bromates or perborates.

The compositions of this invention can also be presurised in the form of an aerosol; carbon dioxide, nitrogen, nitrous oxide and volatile hydrocarbons, such as butane, isobutane and propane, or preferably chlorinated or fluorinated hydrocarbons, can be used as the propellent gas.

The compositions according to the invention can contain any other ingredient normally used in cosmetics, such as perfumes, dyestuffs which can serve to colour the composition itself, preservatives, electrolytes, sequestering agents, thickeners, softeners, synergistic agents, foam stabilisers, sun filters and peptising agents, depending on the application envisaged.

The process for the treatment of keratin fibres according to the invention can consist in applying the composition, containing the amphoteric polymer defined above and the anionic polymer defined above, directly to the hair, in particular by shampooing, by colouring the head of hair or by conditioning the hair using the abovementioned compositions.

The association according to the invention can also be formed in situ on the hair by applying, in a first stage, a composition, for example in the form of a prelotion, containing the amphoteric polymer, and in a second stage, a composition, such as a shampoo or a dye composition, containing the anionic polymer.

According to another embodiment of the invention, it is possible to apply, in a first stage, a shampoo containing the amphoteric polymer, and, in a second stage, a composition, such as a lotion, containing the anionic polymer.

Another possible procedure consists in successively using, in a first stage, a first shampoo containing the amphoteric polymer, and, in a second stage, a second shampoo containing the anionic polymer, it being possible for the pH values of the compositions applied in these two stages to be different and to be adjusted so that, at the moment of the application of the composition containing the anionic polymer, the conditions are such that they permit a good deposition of the combination, according to the invention, on the hair.

The invention also provides a process for curling or straightening the hair, which consists in applying, in a first stage, a reducing composition containing the anionic polymer/amphoteric polymer combination and, in a second stage, the neutralising composition.

According to a modified embodiment, it is possible to apply, in a first stage, the reducing composition containing the amphoteric polymer (or polymers), and in a second stage, the neutralising composition containing the anionic polymer (or polymers).

The process of the present invention can also be regarded as a process for attaching anionic polymers to keratin fibres, in which the attachment is caused by associating it with an amphoteric polymer which is either present in the same composition or has been applied to the keratin fibres beforehand.

The following Examples further illustrate the present invention. Amounts are expressed by weight of active ingredient.

EXAMPLES 1-8

The following composition is prepared:

| | |
|---|---|
| AMPHOMER | 1 g |
| Anionic polymer referred to as 28-29-30 | 0.6 g |
| Non-ionic surface-active agent referred to as TA-1 | 8 g |
| Sandopan DTC-AC | 2 g |
| Hydrochloric acid q.s.p. pH 6.7 | |
| Water q.s.p. | 100 g |

This composition is used as a shampoo.

The hair is easy to comb out when wet. After drying, the hair is bulky and springy and the style holds well with time.

Several successive applications of shampoo do not give rise to disadvantages of roughness or covering.

Similar results could be observed for the compositions (2 to 8) of Table I.

TABLE I
SHAMPOOS

| Example No. | POLYMER AMPHOTERIC | % | ANIONIC | % | SURFACE-ACTIVE AGENT | % | SOLVENTS and/or ADJUVANTS | % | pH | Acidifying or alkalising agent |
|---|---|---|---|---|---|---|---|---|---|---|
| 2 | PAM-1 | 0.8 | Darvan No. 7 | 1 | Akypo RLM 100 | 4 | | | 7.8 | Sodium hydroxide |
| | | | | | TAS 12-14 | 8 | | | | |
| 3 | CHIT | 0.4 | Darvan No. 1 | 0.7 | TA-1 | 8 | | | 6.7 | Hydrochloric acid |
| | | | | | AES | 1 | | | | |
| 4 | PAM-2 | 0.05 | Flexan 130 | 0.2 | Triethanolamine lauryl-sulphate | 2.5 | | | 8 | Sodium hydroxide |
| | | | | | Aromox DMMCD/W | 5 | | | | |
| 5 | PAM-2 | 0.1 | Hydagen F | 0.3 | TA-1 | 10 | | | 8 | Sodium hydroxide |
| | | | | | Akypo RLM 100 | 5 | | | | |
| 6 | PAM-3 | 0.2 | Versicol E.5 | 0.4 | Miranol C.2M | 7.6 | Sodium chloride | 3 | 7.6 | Hydrochloric acid |
| | | | | | TA-3 | 2.4 | | | | |
| 7 | Amphomer | 1.5 | Versicol K.11 | 4 | AES | 2 | | | 8 | Sodium hydroxide |
| | | | | | TAS 12-14 | 10 | | | | |
| 8 | Amphomer | 2 | Goodrite K.752 | 3 | Aromox DM14D/W | 10 | | | 8.8 | Sodium hydroxide |
| | | | | | TAS 12-14 | 25 | | | | |

EXAMPLES 9-20

The following composition is prepared:

| | |
|---|---|
| Amphoteric polymer sold under the name Amphomer | 0.8 g |
| Anionic polymer sold under the name Hydagen F | 1.2 g |
| Surface-active agent referred to as CSA 15 EO | 3 g |
| Surface-active agent referred to as CSA PO | 1.5 g |
| Polawax GP 200 | 2.0 g |
| PEG 6000 distearate | 0.5 g |
| Cellosize QP 4400 H | 0.8 g |
| Ammonyx 4002 | 2 g |

| | |
|---|---|
| Lexein A.510 | 1.4 g |
| Lactac acid q.s.p. pH 5.6 | |
| Water q.s.p. | 100 g |

This composition is applied to hair which has been washed and towel-dried. After an interval of a few minutes, the hair is rinsed. When wet, the hair is soft and easy to comb out. When dry, the hair is easy to style and holds well with time.

Similar results are obtained with the compositions of Examples 10 to 20 of Table II.

TABLE II

| Example No. | POLYMER AMPHOTERIC | % | ANIONIC | % | SURFACE-ACTIVE AGENT | % | SOLVENTS and/or ADJUVANTS | % | pH | Acidifying or alkalising agent |
|---|---|---|---|---|---|---|---|---|---|---|
| 10 | Amphomer | 1 | 28-29-30 | 0.9 | CSA PO | 2 | Polawax GP200 | 3.5 | 6 | Hydrochloric acid |
| | | | | | | | Ammonyx 4002 | 2 | | |
| | | | | | | | Lexein X.250 | 0.85 | | |
| 11 | CHIT | 0.7 | Darvan No. 7 | 1.2 | | | | | 7.5 | Hydrochloric acid |
| 12 | Amphomer | 0.6 | Hydagen F | 1 | | | Lexein S.620 | 1.6 | 7 | Lactic acid |
| 13 | Amphomer | 0.35 | 28-29-30 | 0.4 | | | Lexein X.250 | 0.85 | 7 | Lactic acid |
| 14 | PAM-2 | 0.8 | Hydagen F | 0.7 | CSA PO | 1.5 | Ammonyx 4002 | 3 | 5.7 | Hydrochloric acid |
| | | | | | CSA 15 EO | 2 | Lexein S.620 | 0.7 | | |
| 15 | PAM-2 | 0.9 | Darvan No. 1 | 1 | | | Lexein X.250 | 0.5 | 5 | Hydrochloric acid |
| 16 | PAM-2 | 0.7 | Goodrite K.722 | 0.3 | | | Lexein S.620 | 0.29 | 5.6 | Hydrochloric acid |
| 17 | PAM-2 | 0.6 | Hydagen F | 1.2 | | | Lexein S.620 | 1 | 6 | Hydrochloric acid |
| | | | | | | | Lexein X.250 | 0.5 | | |
| 18 | AM | 0.4 | Darvan No. 7 | 0.7 | | | | | 6.6 | Hydrochloric acid |
| 19 | AM | 1 | 28-29-30 | 0.6 | CSA PO | 2 | Cellosize QP 4400H | 0.8 | 5.5 | Hydrochloric acid |
| | | | | | CSA 15 EO | 3 | Ammonyx 4002 | 2 | | |
| | | | | | | | Lexein X.250 | 0.8 | | |
| 20 | CHIT | 0.09 | Versicol E.5 | 0.02 | | | | | 7.1 | Hydrochloric acid |

On applying the compositions of Examples 11, 18 and 20 in the form of wavesetting lotions, without subsequent rinsing, it is found that the hair holds well and is easy to comb out.

EXAMPLE 21

A shampoo having the following composition is applied in a first stage:

| | |
|---|---|
| PAM-2 | 0.7 g |
| Surface-active agent referred to as TA-2 | 15 g |
| Surface-active agent referred to as TA-1 | 3 g |
| Water q.s.p. | 100 g |
| pH 6.4 (HCl) | |

An aqueous lotion having the following composition is applied in a second stage:

| | |
|---|---|
| VERSICOL E.5 | 0.65 g |
| NATROSOL 250 HHR | 0.3 g |
| Water q.s.p. | 100 g |
| pH 6 (HCl) | |

In the above Examples, the tradenames and the abbreviations used denote the following products:

PAM-1: polymer resulting from the reaction of the polymer PAA-1 with propane-sultone in proportions of 50%.

PAA-1: polyaminoamide resulting from the condensation of adipic acid and diethylenetriamine in equimolecular amounts and crosslinked with epichlorohydrin at a rate of 11 mols of crosslinking agent per 100 amine groups of the polyaminoamide.

PAM-2: polymer resulting from the reaction of the polymer PAA-1 with sodium chloroacetate.

AMPHOMER: octylacrylamide/acrylate/butylaminoethyl methacrylate copolymer sold by National Starch.

AM: polymer of the formula:

$$\left[ -CH-CH_2-CH-CH- \atop {\underset{COOH}{|}} \quad {\underset{CO-NH-(CH_2)_3-N(C_2H_5)_2}{|}} \atop {\overset{CH_3}{\underset{|}{\overset{|}{O}}}} \right]_n$$

PAM-3: polymer resulting from the reaction of the polymer PAA-1 with propane-sultone. (100%)

CHIT: polymer containing the units $$\text{CH}_2\text{OH group with NH-CO-CH}_2-\text{CH}_2-\text{COOH} \quad \text{and} \quad \text{CH}_2\text{OH group with NH}_2$$

in proportions of about 50/50.

28-29-30: vinyl acetate/crotonic acid/vinyl neodecanoate terpolymer sold by National Starch.

HYDAGEN F: sodium salt of polyhydroxycarboxylic acid, sold by Henkel.

DARVAN No.7: sodium polymethacrylate sold by the Société Van der Bilt.

DARVAN No.1: sodium salt of a polymerised alkylnaphthalenesulphonic acid, sold by the Van der Bilt.

GANTREZ ES 425: monobutyl ester of poly-(methyl vinyl ether/maleic acid), sold by the General Anilin.

FLEXAN 130: sodium salt of polystyrenesulphonic acid, having a molecular weight of the order of 100,000 and sold by National Starch.

VERSICOL E.5: mixture of acrylic acid homopolymer and copolymer, having a viscosity of 16 cps in 25% strength solution and a molecular weight of about 3,500 and sold by Allied Colloids.

VERSICOL K.11: methacrylic acid polymer having a molecular weight of 10,000 and a viscosity of 1,000 cps in 25% strength solution and sold by Allied Colloids.

GOODRITE K.752: polyacrylic acid having a molecular weight of 1,800 and sold by Goodrich.

GOODRITE K.722: polyacrylic acid having a molecular weight of 45,000 and sold by Goodrich.

AES: sodium salt of a sulphated alcohol($C_{12}$-$C_{14}$) oxyethyleneated with 2.2 mols of ethylene oxide.

TA-1: non-ionic surface-active agent of the formula:

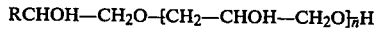

In which R = $C_9$-$C_{12}$ alkyl and n has an average statistical value of 3.5.

TA-2: non-ionic surface-active agent of the formula:

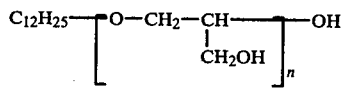

in which n has an average statistical value of 4.2.

TA-3: mixture of polyglycerolated fatty diglycolamides of the formula:

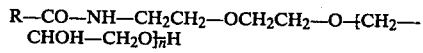

in which n has an average statistical value of 3.5 and R = mixture of radicals derived from natural $C_{12}$ to $C_{18}$ fatty acids.

MIRANOL C.2M: cycloimidazoline derivative of coconut oil, sold by Miranol:

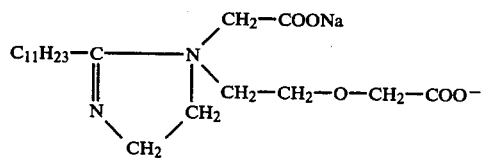

SANDOPAN DTC-AC: trideceth-7 carboxylic acid of the formula: $CH_3(CH_2)_{11}$—$CH_2$—$(OCH_2$—$CH_2$-$)_6OCH_2$—COOH, sold by SANDOZ.

POLAWAX GP 200: mixture of fatty alcohols and oxyethyleneated products, sold by Croda.

CELLOSIZE QP 4400 H: hydroxyethylcellulose having a viscosity of 4,400 cps in 2% strength aqueous solution at 25° C., measured using a Brookfield No. 4 module.

AMMONYX 4002: stearyldimethylbenzylammonium chloride sold by Franconyx.

LEXEIN A.510: product resulting from the condensation of abietic acid and a collagen hydrolysate, sold by Inolex.

LEXEIN X.250: hydrolysate of proteins derived from collagen, sold by Wilson.

LEXEIN S.620: potassium salt of a product resulting from the condensation of collagen proteins and coconut fatty acid, having a molecular weight of 700-800 and sold by Inolex.

CSA 15 EO: oxyethyleneated cetyl/stearyl alcohol containing 15 mols of ethylene oxide.

AKYPO RLM 100: surface-active agent of the formula: R—$(OCH_2CH_2)_{10}OCH_2COOH$, in which R is a mixture of $C_{12}$-$C_{14}$ alkyl radicals, sold by Chem Y.

TAS 12-14: triethanolamine alkyl($C_{12}$-$C_{14}$)-sulphate.

AROMOX DM14D/W: denotes the compound of the formula:

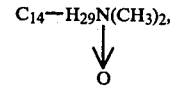

sold by AKZO CHEMIE.

NATROSOL 250 HHR: hydroxyethylcellulose sold by HERCULES.

CSA PO: mixture of cetyl/stearyl alcohol and oxyethyleneated cetyl/stearyl alcohol containing 15 mols of ethylene oxide.

AROMOX DMMCD/W: alkyldimethylamine oxide (alkyl derived from coconut oil) sold by AKZO Chemie.

The disclosure of the patent specifications referred to herein are hereby all incorporated by reference.

We claim:

1. A composition suitable for application to hair fibres which comprises, in a suitable carrier or diluent:
    (a) at least one anionic polymer containing one or more carboxylic or sulphonic groups, said anionic polymer having a molecular weight of from about 500 to 5 million; and
    (b) at least one amphoteric polymer containing units A and B distributed in the polymer chain, where A denotes a unit derived from a monomer containing at least one basic nitrogen atom and B denotes a unit derived from an acid monomer containing one or more carboxyl or sulphonyl groups, or A and B denote a group derived from a zwitterionic carboxybetaine monomer, or A and B denote a cationic polymer chain containing secondary amine groups, tertiary amine groups other than a piperazinyl group, or quaternary ammonium groups, in which chain at least one of the amine groups carries a carboxyl or sulphonyl group joined via a hydrocarbon radical, or A and B form part of a polymer with alpha, beta-dicarboxyethylene units, in which one of the carboxyl groups has been reacted with a polyamine containing one or more primary, secondary or tertiary amine groups, with the proviso that when A and B form a polymer chain comprising polyaminoamide units in which at least one of the amino groups is substituted by a sulphonic or carboxylic acid group via an intermediate hydrocarbon radical, the anionic polymer is not a vinyl acetate/crotonic acid copolymer, said amphoteric polymer having a molecular weight of from about 500 to 2 million, said anionic and said amphoteric polymers each being present in an amount from about 0.01 to about 10% by weight, and with the further proviso that the composition does not contain a cationic polymer.

2. A composition according to claim 1 in which the amphoteric polymer is selected from:

(1) a polymer resulting from the copolymerisation of a vinyl monomer carrying a carboxyl group, and a basic substituted vinyl monomer containing at least one basic nitrogen atom, (2) a polymer containing units derived from
 (a) at least one acrylamide or methacrylamide substituted on the nitrogen by an alkyl radical,
 (b) at least one acid comonomer containing one or more reactive carboxyl groups, and
 (c) at least one basic acrylic or methacrylic comonomer with a primary, secondary or tertiary amine substituent or a quaternary ammonium substituent or the product resulting from the quaternisation of dimethylaminoethyl methacrylate with dimethyl or diethyl sulphate.

(3) a crosslinked and alkylated polyaminoamide partially or totally derived from a polyaminoamide of the general formula:

(I)

in which R represents a divalent radical derived from a saturated dicarboxylic acid or a dicarboxylic aliphatic acid with an ethylenic double bond, or a radical derived from the addition of a said acid or a monocarboxylic acid with an ethylenic double bond onto a bis-primary or bis-secondary amine, and Z denotes a bis-primary or mono- or bis-secondary polyalkylene-polyamino radical, said polyaminoamide having been crosslinked by a difunctional crosslinking agent which is an epihalogenohydrin, diepoxide, dianhydride or bis-unsaturated derivative, using 0.025 to 0.35 mol of crosslinking agent per amine group of the polyaminoamide, and having been alkylated by reaction with acrylic acid, chloroacetic acid or an alkane-sultone or a salt thereof in which case the anionic polymer is other than a vinyl acetate/crotonic acid copolymer.

(4) a polymer containing zwitterionic units, derived from the formula:

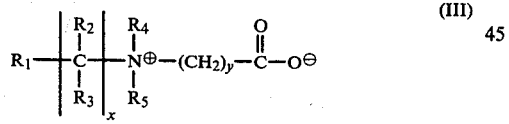
(III)

in which $R_1$ denotes a polymerisable unsaturated group, x and y independently represent an integer from 1 to 3, $R_2$ and $R_3$ independently represent hydrogen, methyl, ethyl or propyl, and $R_4$ and $R_5$ independently represent a hydrogen atom or an alkyl radical such that the sum of the carbon atoms in $R_4$ and $R_5$ does not exceed 10, (5) a polymer derived from chitosan and containing monomer units corresponding to the following formulae:

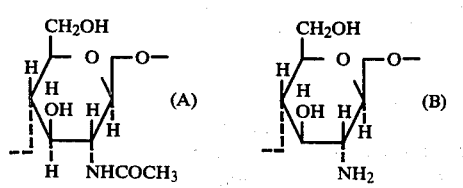

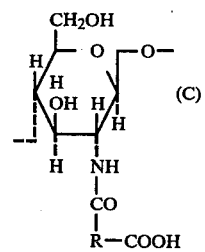

in which the relative proportions of the units are 0 and 30% of unit (A), 5 to 50% of unit (B) and 30 to 90% of unit (C), and R represents the radical of the formula:

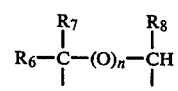

in which, if n is equal to 0, $R_6$, $R_7$ and $R_8$, which are identical or different, each represents a hydrogen atom, a methyl, hydroxyl, acetoxy or amino radical, a monoalkylamino radical or a dialkylamino radical, which may contain one or more chain nitrogen atoms is substituted by one or more amino, hydroxyl, carboxyl, alkylthio or sulphonyl groups, or an alkylthio radical in which the alkyl group carries an amino radical, at least one of the radicals $R_6$, $R_7$ and $R_8$ in this case being a hydrogen atom, or, if n is equal to 1, $R_6$, $R_7$ and $R_8$ each represent a hydrogen atom, or a basic or acid salt of a said polymer, (6) a polymer corresponding to the general formula (IV):

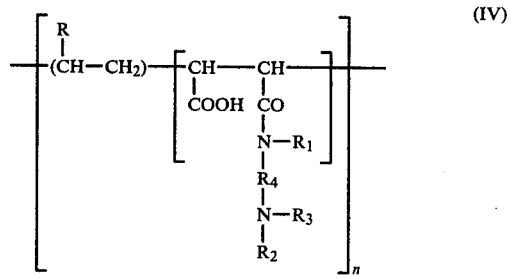
(IV)

in which R represents a hydrogen atom or a CH$_3$O, CH$_3$CH$_2$O or phenyl radical, $R_1$ denotes hydrogen or an alkyl radical of 1 to 6 carbon atoms, $R_2$ denotes hydrogen or an alkyl radical of 1 to 6 carbon atoms, $R_3$ denotes an alkyl radical of 1 to 6 carbon atoms or a radical of the formula: $R_4$—N($R_2$)$_2$, where $R_4$ represents a group —CH$_2$—CH$_2$—, —CH$_2$—CH$_2$—CH$_2$— or

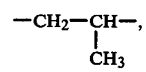

or a higher homologue of said radicals containing up to 6 carbon atoms.

3. A composition according to claim 2 in which polymer (1) is derived from acrylic, methacrylic, maleic or alpha-chloroacrylic acid and form a dialkylaminoalkyl methacrylate or acrylate or a dialkylaminoalkylmethacrylamide or acrylamide.

4. A composition according to claim 2 in which the polymer (4) is one in which at least one of $R_1$, $R_2$ and $R_3$ denotes a methyl or ethyl radical.

5. A composition according to claim 2 in which the amphoteric polymer is a polymer of groups (2), (4), (5) or (6).

6. A composition according to claim 1 in which the carboxyl groups of the anionic polymer are derived from an unsaturated monocarboxylic or dicarboxylic acid of the formula:

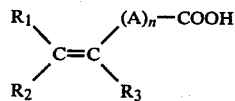

$$\begin{matrix} R_1 & & (A)_n-COOH \\ & C=C & \\ R_2 & & R_3 \end{matrix} \quad (V)$$

in which n is an integer from 1 to 10, A denotes a methylene group either joined directly to the carbon atom of the unsaturated group, or to an adjacent methylene group if n is greater than 1, via a hetero-atom, $R_1$ denotes a hydrogen atom or a phenyl or benzyl group, $R_2$ denotes a hydrogen atom or an alkyl group of 1 to 6 carbon atoms or a carboxyl group, and $R_3$ denotes a hydrogen atom or an alkyl group of 1 to 6 carbon atoms, —$CH_2$—COOH, phenyl or benzyl group.

7. A composition according to claim 6 in which the anionic polymer is selected from:
(a) an acrylic or methacrylic acid homopolymer or copolymer or a salt thereof;
(b) a copolymer of acrylic or methacrylic acid and a monoethylenic unsaturated monomer;
(c) a copolymer derived from crotonic acid;
(d) a polymer derived from maleic, fumaric or itaconic acid or anhydride with a vinyl ester, vinyl ether, vinyl halide, phenylvinyl derivative, and acrylic acid or an ester thereof or esterified forms of said polymers;
(e) a copolymer of maleic, citraconic or itaconic anhydride and an allyl or methallyl ester, or said copolymer containing an acrylamide or methacrylamide group and mono-esterified or mono-amidated;
(f) a salt of polystyrenesulphonic acid;
(g) a salt of lignin sulphonic acid; and
(h) a salt of an alkylnaphthalenesulphonic acid.

8. A composition according to claim 2 in which the amphoteric polymer is a polymer of group 2 or group 5 and the anionic polymer is selected from:
an acrylic or methacrylic acid homopolymer or copolymer or a salt thereof,
a polymer derived from maleic acid or anhydride, and
a salt of polystyrenesulphonic acid.

9. A composition according to claim 1 in which the amphoteric polymer is an octylacrylamide/acrylate/-butylaminoethyl methacrylate copolymer and the anionic polymer is the sodium salt of a polyhydroxycarboxylic acid, methacrylic acid polymer, a mixture of acrylic acid homopolymer and copolymer, the sodium salt of a polystyrene sulphonic acid or the monobutyl ester of poly-(methyl vinyl ether/maleic acid).

10. A composition according to claim 1 which has a pH of 2 to 11.

11. A composition according to claim 1 which contains at least one monoalcohol, polyalcohol or glycol ether as solvent.

12. A composition according to claim 1 which contains at least one anionic, cationic, non-ionic or amphoteric surface-active agent or mixture thereof.

13. A composition according to claim 1 which is in the form of an aqueous, alcoholic or aqueous-alcoholic solution, a gel, a thickened lotion, an emulsion, a cream or a powder.

14. A composition according to claim 1 which contains at least one dyestuff for colouring the composition or the fibres treated, a preservative, sequestering agent, thickener, softener, synergistic agent, foam stabiliser, sun filter or peptising agent.

15. A composition according to claim 1 which contains at least one electrolyte.

16. A composition suitable for conditioning of human hair, which comprises at least one amphoteric polymer of groups (1), (2), (4), (5) or (6) as defined in claim 2, at least one anionic polymer containing one or more carboxyl or sulphonyl groups, and at least one adjuvant suitable for application to the hair.

17. Process for the conditioning of hair fibres, which comprises applying thereto at least one composition as defined in claim 1.

18. Process according to claim 17 which comprises after allowing the composition to impregnate the fibres, rinsing the fibres.

19. Process for the conditioning of hair fibres, which comprises applying, in a first stage, a composition containing an amphoteric polymer as defined in claim 1 and, in a second stage, a composition containing an anionic polymer as defined in claim 1.

20. A composition suitable for application to hair which comprises, in a suitable carrier or diluent:
(I) at least one amphoteric polymer which is
(1) a polymer resulting from the copolymerisation of a vinyl monomer carrying a carboxylic group and a basic monomer which is a substituted vinyl compound containing at least one basic nitrogen atom of the group comprising dialkylaminoalkyl methacrylates or acrylates or dialkylaminoalkyl-methacrylamides or -acrylamides;
(2) a polymer containing units derived from
(a) at least one monomer selected from acrylamides or methacrylamides substituted on the nitrogen by an alkyl radical containing 2 to 12 carbon atoms,
(b) at least one acid comonomer containing one or more reactive carboxylic groups,
(c) at least one basic comonomer comprising esters with primary, secondary or tertiary amine substituents or quaternary ammonium substituents, of acrylic and methacrylic acids, of the product resulting from the quaternisation of dimethylaminoethyl methacrylate with dimethyl or diethyl sulphate;
(3) a crosslinked and alkylated polyaminoamide partially or totally derived from polyaminoamides of the general formula:

$$-[OC-R-CO-Z]- \quad (I)$$

in which R represents a divalent radical derived from a saturated dicarboxylic acid, from a monocarboxylic or dicarboxylic aliphatic acid with an ethylenic double bond, or from an ester of a lower alkanol having 1 to 6 carbon atoms of these acids or of a radical derived from the addition of any one of the said acids onto a bis-primary or bis-secondary amine, and Z denotes a radical of a bis-primary or mono- or bis-secondary polyalkylene-polyamine, and representing (a) in proportions of 60 to 100 mol %, the radical

in which $x=2$ and $n=2$ or $3$ or $x=3$ and $n=2$, this radical being derived from diethylenetriamine, triethylenetetramine or dipropylenetriamine;

(b) in proportions of 0 to 40 mol %, the above radical (II) in which $x=2$ and $n=1$ which is derived from ethylenediamine, or the radical

derived from piperazine; or (c) in proportions of 0 to 20 mol %, the radical $-NH-(CH_2)_6-NH-$, derived from hexamethylenediamine, these polyaminoamides being crosslinked by the addition of a difunctional crosslinking agent selected from epihalogenohydrins, diepoxides, dianhydrides and bis-unsaturated derivatives, using 0.025 to 0.35 mol of crosslinking agent per amine group of the polyaminoamide, and being alkylated by reaction with acrylic acid, chloroacetic acid or an alkane-sultone or their salts in which case the anionic polymer is other than a vinylacetate/crotonic acid polymer;

(4) a polymer containing zwitterionic units derived from the formula:

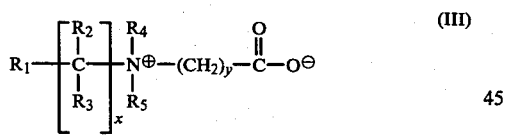

in which $R_1$ denotes a polymerisable unsaturated group of the group comprising an acrylate, methacrylate, acrylamide or methacrylamide group, x and y independently represent an integer from 1 to 3, $R_2$ and $R_3$ independently represent hydrogen, methyl, ethyl or propyl, and $R_4$ and $R_5$ independently represent a hydrogen atom or an alkyl radical such that the sum of the carbon atoms in $R_4$ and $R_5$ does not exceed 10;

(5) the polymers derived from chitosan and containing monomer units corresponding to the following formulae:

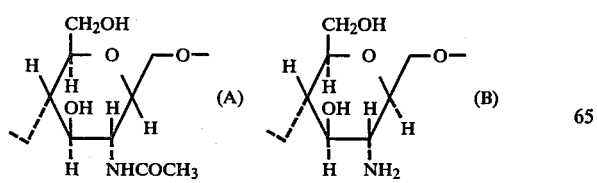

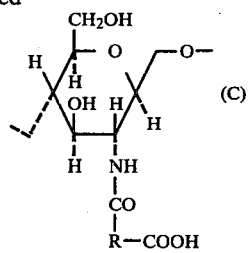

in which the unit A is present in proportions of 0 to 30%, B is present in proportions of 5 to 50% and C is present in proportions of 30 to 90% and in the formula C, R represents a radical of the formula:

in which, if $n=0$, $R_6$, $R_7$ and $R_8$, which are identical or different, each represent a hydrogen atom, a methyl, hydroxyl, acetoxy or amino radical, a monoalkylamino radical or a dialkylamino radical, which may be interrupted by one or more nitrogen atoms or substituted by one or more amine, hydroxyl, carboxyl, alkylthio or sulphonyl groups, or an alkylthio radical in which the alkyl group carries an amino radical, at least one of the radicals $R_6$, $R_7$ and $R_8$ in this case being a hydrogen atom, or, if n is equal to 1, $R_6$, $R_7$ and $R_8$ each represent a hydrogen atom or their salts;

(6) a polymer corresponding to the general formula:

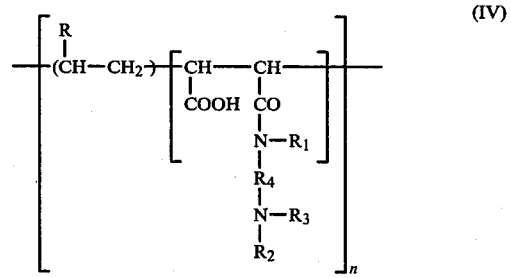

in which R represents a hydrogen atom or a $CH_3O$, $CH_3CH_2O$ or phenyl radical, $R_1$ denotes hydrogen or a lower alkyl radical, $R_2$ denotes hydrogen or a lower alkyl radical, $R_3$ denotes a lower alkyl radical or a radical corresponding to the formula $R_4-N(R_2)_2$, where $R_4$ represents a group $-CH_2-CH_2-$, $-CH_2-CH_2-CH_2-$ or

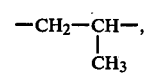

or the higher homologues of these radicals containing up to 6 carbon atoms; and (II) an anionic polymer containing one or more sulphonic groups or one or more carboxylic groups provided by unsaturated monocarboxylic or dicarboxylic acids having the formula:

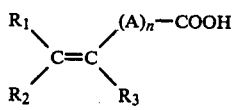

in which n is 0 or an integer from 1 to 10, A denotes a methylene group joined either directly to the carbon atom of the unsaturated group, or to an adjacent methylene group if n is greater than 1, via a hetero-atom, such as oxygen or sulphur, $R_1$ denotes a hydrogen atom or a phenyl or benzyl group, $R_2$ denotes a hydrogen atom or a lower alkyl or carboxylic group, and $R_3$ denotes a hydrogen atom or a lower alkyl, $-CH_2-COOH$, phenyl or benzyl group, said amphoteric polymers having a molecular weight of from about 500 to 2 million, said anionic polymer having a molecular weight of from about 500 to 5 million, said amphoteric and said anionic polymers each being present in an amount from about 0.01 to about 10% by weight.

21. Composition according to claim 20 comprising an anionic polymer selected from the group:
(1) acrylic or methacrylic acid homopolymers or copolymers or their salts, the acrylic acid/acrylamide copolymers or the acrylic or methacrylic acid/vinyl alcohol copolymers;
(2) the copolymers of the above-mentioned acids with a monoethylenic unsaturated monomer comprising ethylene, vinylbenzene, vinyl or allyl esters or acrylic or methacrylic acid esters, which copolymers may be grated onto a polyalkylene glycol or may be crosslinked, or the copolymers of this type which contain an acrylamide or N-alkylated or N-hydroxyalkylated acrylamide unit in their chain;
(3) the copolymers derived from crotonic acid which may contain, in their chain, vinyl acetate or propionate units or from monomers comprising allyl or methallyl ester, vinyl ether or vinyl ester of a saturated carboxylic acid with a long hydrocarbon chain; and the grafted or crosslinked derivatives thereof.
(4) the polymers derived from maleic, fumaric or itaconic acids or anhydrides with vinyl esters, vinyl ethers, vinyl halides, phenylvinyl derivatives, acrylic acid or its esters or esterified forms of these polymers or copolymers of maleic, citraconic or itaconic anhydrides with an allyl or methallyl ester which may contain an acrylamido or methacrylamido group in their chain and are monoesterified or mono-amidated;
(5) the salts of polystyrenesulphonic acid;
(6) the alkali metal or alkaline earth metal salts of the sulphonic acids derived from lignin; or
(7) the polymers containing salified alkylnaphthalenesulphonic acid units.

* * * * *